US009530527B2

(12) United States Patent
Pop et al.

(10) Patent No.: US 9,530,527 B2
(45) Date of Patent: Dec. 27, 2016

(54) ADVANCED FUEL CRUD SAMPLING TOOL METHOD

(75) Inventors: Mihai G. M. Pop, Lynchburg, VA (US); Anthony A. Pugh, Forest, VA (US); Laurence S. Lamanna, Amherst, VA (US); John T. Willse, Lynchburg, VA (US)

(73) Assignee: AREVA Inc., Lynchburg, VA (US)

( * ) Notice: Subject to any disclaimer, the term of this patent is extended or adjusted under 35 U.S.C. 154(b) by 1624 days.

(21) Appl. No.: 12/841,848

(22) Filed: Jul. 22, 2010

(65) Prior Publication Data

US 2011/0019790 A1 Jan. 27, 2011

Related U.S. Application Data

(60) Provisional application No. 61/271,598, filed on Jul. 23, 2009.

(51) Int. Cl.
*G01C 17/00* (2006.01)
*G21C 17/017* (2006.01)
(Continued)

(52) U.S. Cl.
CPC ............... *G21C 17/017* (2013.01); *G01N 1/04* (2013.01); *G01N 23/225* (2013.01); *G21C 17/06* (2013.01);
(Continued)

(58) Field of Classification Search
CPC ....... G21C 17/017; G21C 17/06; G21C 19/00; G01N 23/225; G01N 1/04; G01N 2001/028; G01N 2223/625
(Continued)

(56) References Cited

U.S. PATENT DOCUMENTS 3,806,979 A 4/1974 Bonami et al.
3,871,139 A * 3/1975 Rands ........................... 451/466
(Continued)

FOREIGN PATENT DOCUMENTS

JP 03-82954 4/1991
JP 11-142577 5/1999
(Continued)

OTHER PUBLICATIONS

Chen, Jiaxin, "On the Interaction between Fuel Crud and Water Chemistry in Nuclear Power Plants", SKI report, Jan. 2000.*
(Continued)

*Primary Examiner* — Frank J McGue
(74) *Attorney, Agent, or Firm* — Davidson, Davidson & Kappel, LLC

(57) ABSTRACT

A method to perform an analysis of two types of CRUD on a nuclear fuel rod, including providing a nuclear fuel rod with a first and second layer of CRUD on an exterior of the fuel rod; brushing the first layer of CRUD from the fuel rod with a CRUD tool on a selected area; wherein the tool has a brushing device, a force applied to the brushing device on the fuel rod to remove the first layer of CRUD, the force being sufficient enough to perform such removal; collecting the first layer of CRUD from the brushing device, scraping the second layer of CRUD from the fuel rod in the selected area with the tool, wherein the tool has a scraping device and a second force is applied to the tool for scraping, collecting the second layer of CRUD from the scraping device, and analyzing the first layer and second layer of CRUD separately with a scanning electron microscope.

19 Claims, 3 Drawing Sheets

(51) Int. Cl.
   G21C 17/06    (2006.01)
   G21C 19/00    (2006.01)
   G01N 23/225   (2006.01)
   G01N 1/04     (2006.01)
   G01N 1/02     (2006.01)

(52) U.S. Cl.
   CPC ......... *G21C 19/00* (2013.01); *G01N 2001/028* (2013.01); *G01N 2223/625* (2013.01)

(58) Field of Classification Search
   USPC .......................................... 376/245
   See application file for complete search history.

(56) References Cited

U.S. PATENT DOCUMENTS

| | | | | |
|---|---|---|---|---|
| 4,063,962 | A | * | 12/1977 | Arya et al. .................. 134/8 |
| 4,286,416 | A | * | 9/1981 | Cooper, Jr. .................. 451/466 |
| 4,483,205 | A | | 11/1984 | Bellaiche et al. |
| 4,683,109 | A | * | 7/1987 | Cooper et al. .................. 376/261 |
| 4,877,122 | A | * | 10/1989 | Morin .................. 198/499 |
| 4,925,621 | A | * | 5/1990 | Muth et al. .................. 376/262 |
| 4,987,367 | A | | 1/1991 | Ishikawa et al. |
| 5,838,752 | A | * | 11/1998 | Shimamura .................. 376/260 |
| 7,132,651 | B2 | * | 11/2006 | Pop et al. .................. 250/307 |
| 7,304,301 | B1 | | 12/2007 | Pop et al. |
| 2002/0003853 | A1 | * | 1/2002 | Ohno et al. .................. 376/310 |
| 2002/0015464 | A1 | * | 2/2002 | Bowen et al. .................. 376/310 |
| 2008/0277581 | A1 | * | 11/2008 | Pop et al. .................. 250/307 |
| 2009/0060780 | A1 | | 3/2009 | Walter et al. |
| 2009/0078035 | A1 | | 3/2009 | Mecca et al. |

FOREIGN PATENT DOCUMENTS

| | | |
|---|---|---|
| JP | 2001-281386 | 10/2001 |
| KR | 20070095652 | 10/2007 |

OTHER PUBLICATIONS

Huijbregts et al., "Deposition of CRUD in BWR water on various steels exposed in the Dodewaard nuclear power plant", JAF Conference, Tokyo, 1987.*

Blok et al., Ultrasonic Cleaning of BWR Fuel, EPRI [Technical Update], Dec. 2004.

Janney et al.. Phase Identifications in Crud from Commercial Boiling Water Reactors at the Idaho National Laboratory by Transmission Electron Microscopy, 2007 International LWR Fuel Performance Meeting, Sep. 2007.

* cited by examiner

ADVANCED FUEL CRUD SAMPLING TOOL METHOD

Priority to U.S. Provisional Patent Application Ser. No. 61/271,598 filed Jul. 23, 2009, is claimed, the entire disclosure of which is hereby incorporated by reference.

The present invention relates generally to a CRUD analysis method and tool for nuclear reactors, and more specifically for nuclear fuel rods within the nuclear fuel assemblies housed in the reactor core.

BACKGROUND

In water-cooled reactors, activated corrosion and wear products are dissolved in the water. The solubility of these products varies with reactor conditions, i.e. mainly temperature, pH at a given dissolved $H_2$ concentration, and chemistry of the primary coolant, all of which may change along the coolant circuit and during the fuel cycle. These variations cause metallic material dissolution at one point of the primary coolant circuit and deposition onto the circuit surfaces at another. The deposits are generally generated by precipitation reactions and are usually made of solid particles, agglomerated together that can be strongly attached to the underlying substrate. The term CRUD, an acronym for Chalk River Unidentified Deposits, is commonly used to characterize these deposits. CRUD deposition is temperature dependent and tends to deposit more rapidly at the highest temperature surfaces further exacerbating the condition. In the nuclear reactor circuit, the highest temperature surfaces are the nuclear fuel rod claddings. As thermal and hydraulic conditions play a major role in the deposition, within the reactor core deposits can be expected at sub-cooled nucleate boiling regions, this mechanism favoring the impurities concentration and the solubility decrease, at higher temperature surface locations, at low turbulence regions, and at high impurity concentration locations in the primary coolant. As time passes, materials can collect on an exterior oxidized surface of the zirconium base alloy claddings of the nuclear fuel rods that contain the fissile material such as enriched uranium dioxide or mixed oxide made of uranium dioxide and plutonium dioxide. CRUD buildup on fuel rod claddings reduces the heat transfer coefficient from the fuel rod surface to the primary coolant resulting in higher fuel rod temperature and as such in increased oxidation of the zirconium cladding. Thicker local CRUD allows specie precipitation, such as boron, which, if exceeding a given quantity per unit area of fuel rod, could lead to local nuclear power shifts.

To perform analysis of CRUD deposited on the fuel assemblies, samples must be taken by mechanically brushing or scraping the exterior of the fuel rods. The systems used to perform this mechanical brushing consist of a mechanical arm having at one end a rotating brush of a given configuration and bristle material. The mechanical brush brushes the surface of the CRUD, collecting, depending on the pressure applied to the arm and the selection of bristle materials, part or all of the CRUD deposit. The systems to perform the mechanical scraping include a rigid member that the fuel rod is pressed against, thereby shearing the loose CRUD from the rest of the nuclear fuel rod when the rigid member is moved over the fuel rod. Another method used to collect CRUD deposits is the rotating wheel scraping method where a highly abrasive material wheel is pressed while rotating against the surface of the fuel rod. All of the above mechanisms are embodied in a manual or mechanical device.

More specifically, CRUD is a non-homogeneous material and porosity changes in the thickness of the deposit. Usually the small thickness deposits and the exterior of the higher thickness deposits are characterized by a relatively high porosity in the order of 70% to 80%, and higher, having a fluffy friable aspect. In case of thick deposition, up to 60% of the deposit thickness may be tenacious with porosity less than 50%. The CRUD composition can highly affect the fuel rod cladding corrosion locally, either by acting as a thermal insulator or by chemically favoring the corrosion process. The knowledge of elemental distributions at various locations of the cross-section of the CRUD (Fe, Cr, Ni, Co, Si, Zn, etc.), of the individual crystal chemistry, of the size and morphology of the crystals is of fundamental importance to define a suitable surveillance scheme. As such a method is needed that allows a differentiate collection of CRUD, better responding to the porosity and density characteristics of the deposition and also providing better answers on what quantities and what type of CRUD material can be entrained during start-up or during sequence exchange (fluffy CRUD) and what quantity and type of CRUD remains attached to the pin surface irregardless of the operating conditions.

Existing devices have a major drawback that limit the effectiveness of the CRUD analysis: fluffy and tenacious CRUD are collected together leading to mixing of samples and losing important information needed to define the best surveillance scheme and associated action plan for the further operation of the nuclear reactor.

U.S. Pat. No. 7,132,651, incorporated herein by reference, teaches a method for collection and analysis of CRUD flakes.

SUMMARY OF THE INVENTION

There is a need to provide a CRUD removal method which will allow for separate collection and analysis of fluffy CRUD and tenacious CRUD on an exterior of a nuclear fuel rod.

There is also a need to provide a CRUD removal method which will allow separate collection of fluffy and tenacious CRUD on the same geometrical surface of the exterior of the nuclear fuel rod.

An object of the present invention is to provide a method of CRUD analysis combining a brushing and scraping tool for nuclear fuel rods to determine the physical properties of the CRUD deposited on an exterior of a nuclear fuel rod allowing for the separation in both collection and analysis of fluffy CRUD and tenacious CRUD.

The present invention provides a method to perform an analysis of two types of CRUD on a nuclear fuel rod, comprising: providing a nuclear fuel rod with a first and second layer of CRUD on an exterior of the fuel rod, brushing the first layer of CRUD from the fuel rod with a CRUD tool on a selected area, wherein the tool has a brushing device, a force applied to the brushing device on the fuel rod being defined to allow removal of the first layer of CRUD, collecting the first layer of CRUD from the brushing device, scraping the second layer of CRUD from the fuel rod in the selected area with the tool, wherein the tool has a scraping device, a force applied to the scraping device on the fuel rod being defined to allow removal of the second layer of CRUD, collecting the second layer of CRUD from the scraping device, and analyzing the first layer and second layer of CRUD with a scanning electron microscope.

BRIEF DESCRIPTION OF THE DRAWINGS

Preferred embodiments of the present invention will be described with respect to the drawings in which.

DETAILED DESCRIPTION OF THE DRAWINGS

Figure 1:
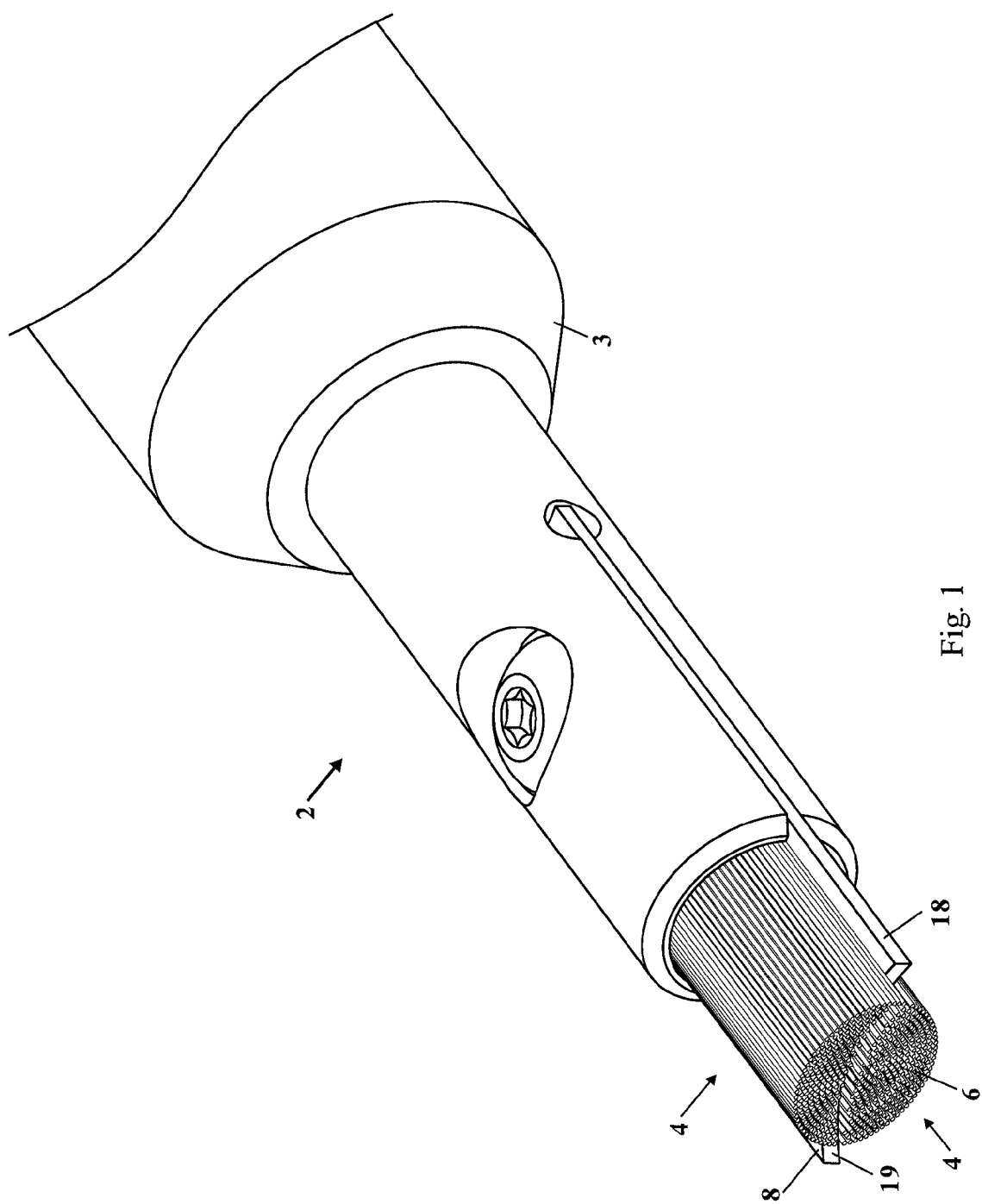
FIG. 1 shows a brush/scraping tool in conformance with a first embodiment of the present invention.

FIG. 1 shows a first embodiment of a CRUD brushing/scraping tool 2 designed to perform fuel CRUD sampling via a two step process. Tool 2 includes a tool head 3 housing a brushing device 4 and scraping device 8. Scraping device 8 has a blade 18. Brushing device 4 has plastic bristles 6 which extend from the face 19 of blade 18 so that a two stage brush/scrape method can be performed. In the illustrated embodiment, scraping device 8 and brushing device 4 are fixed with respect to each other. Tool head 3 has the capability to house other tools such as an abrasive material wheel.

Figure 2:
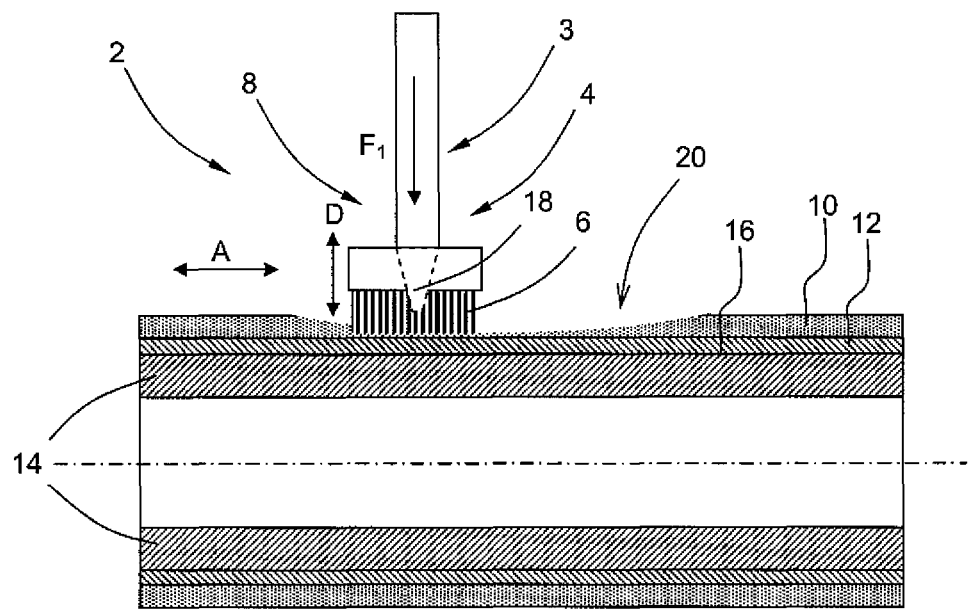
FIG. 2 shows a brushing device of the tool applied to a fuel rod according to a second embodiment of the invention.

FIG. 2 shows a surface of a fuel rod 14 covered with a first layer 10 of fluffy CRUD and a second layer 12 of tenacious CRUD. Brushing device 4 is used to remove first layer 10 of fluffy CRUD from a selected surface 20 of the fuel rod 14 by brushing it away, scraping device 8 being retracted. Brushing device 4 moves back and forth as depicted by arrows A, moving bristles 6 in a back and forth movement on selected surface 20 of the fuel rod 14 to obtain an initial sample and remove loose first layer 10 of fluffy CRUD with no blade contact. A given force F1 is applied on tool 2 to engage bristles 6 of brushing device 4 on selected surface 20. The amount of pressure applied is defined to allow a timely and successful removal of the fluffy deposit without contact of blade 18 with first layer 10. F1 may range between 2 and 60 psi. Bristles 6 clean first layer 10 of fluffy CRUD from selected surface 20 of fuel rod 14. Bristles 6 of brushing device 4 are preferably nylon, however a large variety of plastic materials or soft materials are suitable for this application. Other brushing tool configurations may also be used such as rotating disks with plastic bristles or other selected brushing materials. Once removed from fuel rod 14, first layer 10 of fluffy CRUD may be analyzed prior to, in parallel or after the second stage of the process—the scraping. First layer 10 of fluffy CRUD is analyzed individually.

Figure 3:
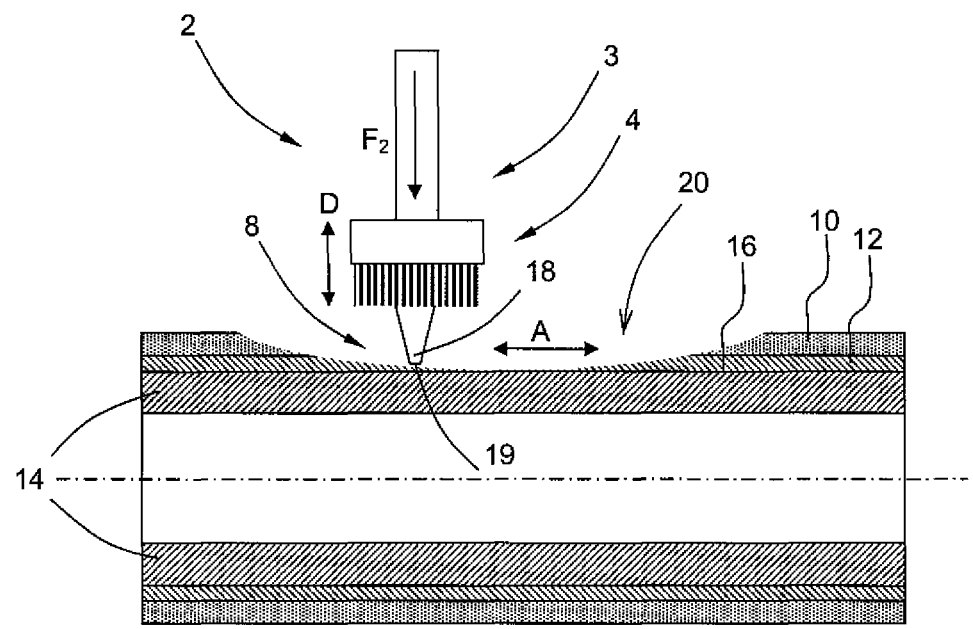
FIG. 3 shows a scraping device of the tool acting on the fuel rod in accordance with the second embodiment.

FIG. 3 shows the scraping device 8 of tool 2 applied to the same previously selected surface 20 on fuel rod 14, brushing device 4 being retracted. In the first embodiment of the invention blade 18 is applied on the selected surface 20 by increasing the contact pressure. In the illustrated second embodiment, brushing device 4 and the scraping device 8 are movable in direction D with respect to each other, in an alternative, they can be moveable in direction A or in any other directions with respect to one another. In first, second and alternate embodiments, tool 2 does not need to be repositioned in between the brushing and scraping stages. First layer 10 of fluffy CRUD has already been removed via brushing device 4. Scraping blade 18 is applied after brushing has occurred on the selected surface 20 of the fuel rod 14. Blade 18 moves back and forth in direction as depicted in FIG. 3 by arrows A. The back and forth movement A occurs on the same selected area 20. The highest tool pressure setting, a given force F2, is applied to tool 2 to assure blade surface 19 of blade 18 is in full contact with selected surface 20 of fuel rod 14 to get a second sample, the second sample being of second layer 12 of tenacious CRUD, with possibly a zirconium oxide layer 16. F2 may range between F1 and 60 psi, and preferably between 15 and 60 psi. Blade 18 is preferably made of rigid material chosen to hinder potential corrosion, for instance, of stainless steel, or preferably of zirconium alloy. The collection of second layer 12 of tenacious CRUD then gets individually analyzed.

Following the brushing and scraping of fuel rod 14, selected surface 20 is visually inspected using underwater video cameras. The visual inspection is recorded and then read by one of skill in the art. If there is substantial second layer 12 of tenacious CRUD remaining, the tool head 3 is configured with an abrasive stone device such as an abrasive material wheel that is engaged with the highest pressure setting F2 to remove all second layer 12 of tenacious CRUD material. The stone device is re-indexed at the same location in which the brushing device and the scraping device performed. The stone device is used until all of second layer 12 of tenacious CRUD and all zirconium oxide layer 16 is removed from the surface of fuel rod 14, and the clean base metal of the surface of fuel rod 14 is visible. Sequences in automaton of tool 2 allow a first deployment of brushing device 4 and a second deployment of scraping device 8 on the same geometrical selected surface 20 of fuel rod 14 with enough time interval in between such as to allow changing of the filter media that collects the two different samples, first layer 10 of fluffy CRUD and second layer 12 of tenacious CRUD, and possibly an ultimate pass on the same surface after the blade scraping, with an abrasive stone device. Obtaining the separate information on the quantity and quality of first layer 10 of fluffy CRUD and second layer 12 of tenacious CRUD provides a better understanding of the CRUD transport phenomena and its effects on the operation of the power plant and on the activity level of the various components of the nuclear power plant.

Brushing first layer 10 of fluffy CRUD with brushing device 4 and following it with a scraping movement with scraping device 8 provides a separation between the collection of first layer 10 of fluffy CRUD and second layer 12 of tenacious CRUD from the same selected surface 20 with capability to obtain precious information on CRUD layer deposition. Such a method of brushing followed by scraping is very valuable at plants where a large portion of the deposit is first layer 10 of fluffy CRUD. This is important in determining the contribution of chemical species in first layer 10 of fluffy CRUD to the transport of chemical species during some operating conditions.

The collected flakes of first layer 10 of fluffy CRUD and second layer 12 of tenacious CRUD are individually sorted into particle fractions and analyzed with a number of analytical tools including a scanning electron microscope (SEM), wherein tool 2 has a brushing device 4 having bristles with an elasticity corresponding to the type of CRUD and scraping device 8 having a blade 18 with a rigidity that is matched to an anticipated CRUD deposit shear strength. The methods of CRUD analysis are the same as that taught in U.S. Pat. No. 7,132,651 which is incorporated by reference. Such methods are briefly discussed below but disclosed further in U.S. Pat. No. 7,132,651. The methods taught in the above mentioned patent are applied to both the first layer 10 of fluffy CRUD and second layer 12 of tenacious CRUD individually.

One such method of analyzing for the present invention includes providing an electron backscatter diffraction (EBSD) apparatus attached to a scanning electron microscope (SEM); and otherwise actuating the SEM apparatus to determine a crystal system, lattice parameter of unit cells and a point of group crystals belonging to an in-situ portion of the flake. The invention also provides a method for analysis of CRUD flake cross-section on a nuclear fuel rod. The invention provides the steps of determining morphology of crystals of the flake, determining size of the crystals of the flake, correlating elemental distributions of the flake at various locations on the flake wherein the distributions are obtained with a SEM with attached energy dispersive spectrometer, determining depletion of iron enrichment and an enrichment in other species such as copper, zinc and silicon in the crystals by the elemental distributions, and correlating the depletion of iron enrichment and the enrichment in other species such as copper, zinc and silicon with the size and the morphology of the crystals.

The SEM may be used in Microscope-Energy Dispersive Spectrometer (SEM/EDS) as discussed further in U.S. Pat. No. 7,132,651. It is used in conjunction with the previously available bulk techniques (ICP, XRD and Gamma Spectrometry) in order to extrapolate and integrate the critical information of local CRUD characteristics in the assembly of the data from CRUD. Flake porosity is estimated based on a SEM image of the flake. Using the method, the porosity of other CRUD flakes may be estimated. CRUD may be much denser in failed regions of nuclear fuel rods than un-failed regions.

Figure 4:
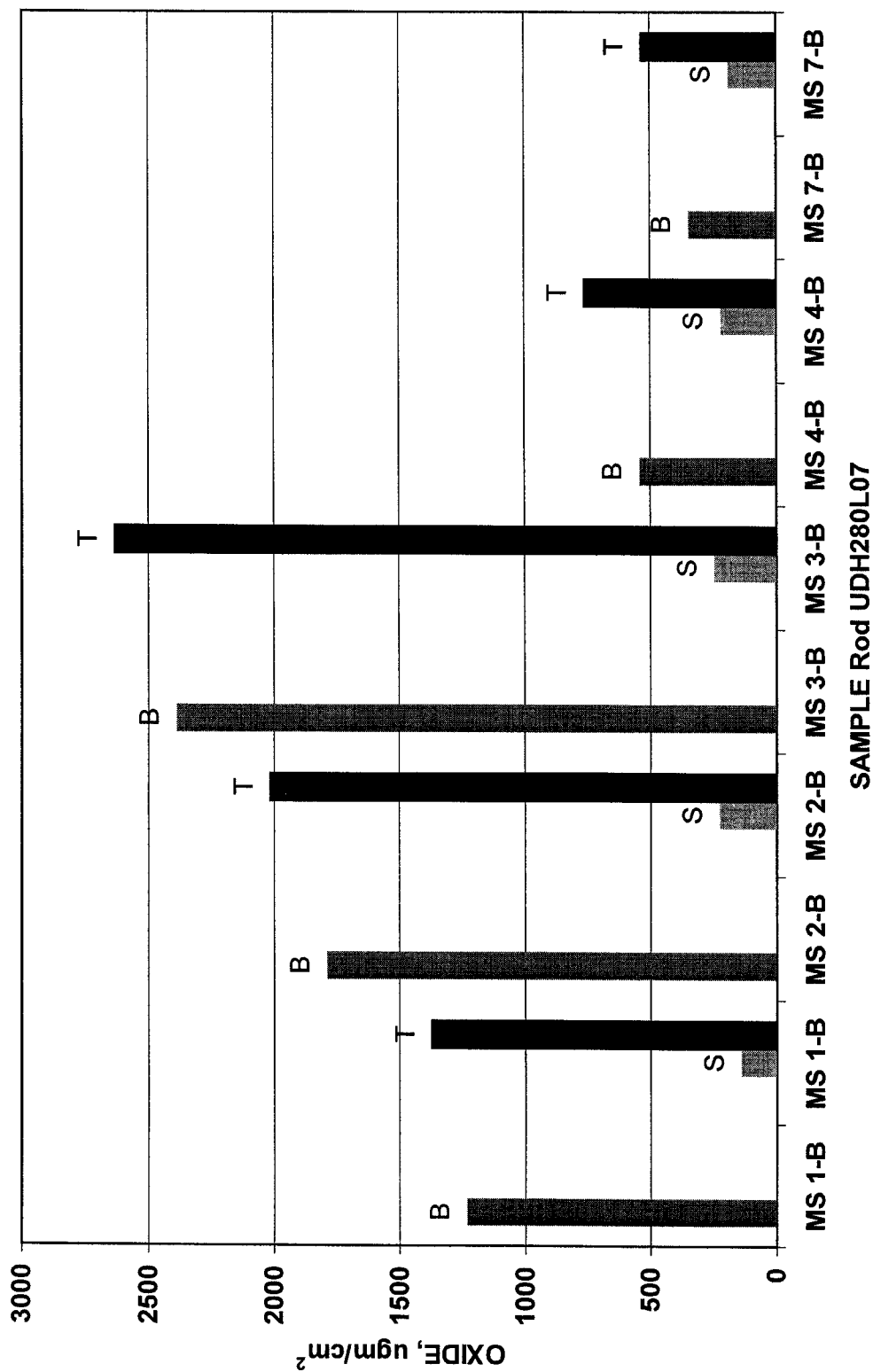
FIG. 4 shows CRUD distribution by fuel rod region in a BWR, with separate fluffy and tenacious CRUD according to the present invention.

The two stage method of the present invention allows a differentiation between the content and quantity of fluffy CRUD between a first irradiated and a second irradiated fuel rods, allowing an assessment of the level of entrainment on the second fuel rod of fluffy CRUD originally deposited on the first fuel rod. The two stage method of the present invention can also be used to understand the transport and entrainment of fluffy CRUD on a third irradiated fuel rod from first and second irradiated fuel rods. FIG. 4 shows that using a new sampling and analysis method of the present invention provides quantitative answers to what CRUD is available for entrainment and what CRUD is tightly adherent to the fuel rods and what is the axial distribution of fluffy and tenacious CRUD. Using a brushing device 4 followed by a scraping device 8 typically removes nearly 100% of the fuel rod deposit; including zirconium oxide near the cladding. In FIG. 4, B corresponds to brushed fluffy CRUD collection, S corresponds to scraped tenacious CRUD collection and T represents the total of the two. The collection is performed on an irradiated fuel rod between two adjacent spacer grids at the mid-span (MS). In the illustrated embodiment, elevation 1 is between the first and the second spacer grids from the bottom of the fuel assembly (MS 1-B) and elevation 7 is between the seventh and the eighth spacer grids from the bottom of the fuel assembly (MS 7-B). The analysis also allows separation of total quantities by type CRUD available for both fluffy and tenacious CRUD. The use of the present invention brushing device 4 followed by scraping device 8 has proven extremely useful in finding the percentage of fluffy CRUD and correlating it to the extent of CRUD redistribution at the beginning of the next irradiation cycle. More CRUD redistribution can potentially result in a heavier load on the fresh fuel assemblies.

In the preceding specification, the invention has been described with reference to specific exemplary embodiments and examples thereof. It will, however, be evident that various modifications and changes may be made thereto without departing from the broader spirit and scope of invention as set forth in the claims that follow. The specification and drawings are accordingly to be regarded in an illustrative manner rather than a restrictive sense.

What is claimed is:

1. A method to perform an analysis of two types of CRUD on a nuclear fuel rod, comprising:
   providing a nuclear fuel rod with a first and second layer of CRUD on an exterior of the fuel rod, the second layer being below the first layer;
   brushing the first layer of CRUD from the fuel rod with a CRUD tool on a selected area; wherein the tool has a brushing device, a force applied to the brushing device on the fuel rod to remove the first layer of CRUD, the force being sufficient enough to perform such removal;
   collecting the first layer of CRUD from the brushing device;
   scraping the second layer of CRUD from the fuel rod in the selected area with the tool, wherein the tool has a scraping device and a second force is applied to the tool for scraping;
   collecting the second layer of CRUD from the scraping device; and
   analyzing the first layer and second layer of CRUD separately with a scanning electron microscope.

2. The method as recited in claim 1 wherein the scraping device has a blade.

3. The method as recited in claim 2 wherein the blade is stainless steel.

4. The method as recited in claim 2 wherein the blade is made of zirconium alloy.

5. The method as recited in claim 1 wherein the brushing device has bristles.

6. The method as recited in claim 5 wherein the bristles are soft or plastic materials.

7. The method as recited in claim 6 wherein the bristles are nylon.

8. The method as recited in claim 1 wherein the scraping device and the brushing device are fixed with respect to each other.

9. The method as recited in claim 1 wherein the scraping device and the brushing device are moveable with respect to one another, the brushing device and the scraping device being retracted when the other is in use.

10. The method as recited in claim 1 further comprising visually inspecting the selected area for remaining CRUD.

11. The method as recited in claim 10 further comprising engaging a stone device after the scraping device if any of the second layer of CRUD material remains on the fuel rod in the selected area, wherein the second force of scraping is applied to the stone device.

12. The method as recited in claim 11 wherein the stone device is a wheel.

13. The method as recited in claim 12 wherein the wheel is made of an abrasive material.

14. The method as recited in claim 1 wherein the second force applied during the scraping of the second layer is higher than the force applied during the brushing of the first layer.

15. The method as recited in claim 14 wherein the force applied to the brushing device is between 2 and 60 psi.

16. The method as recited in claim 14 wherein the second force applied to the scraping device is between 15 and 60 psi.

17. The method as recited in claim 1 further comprising sorting the first layer and second layer CRUD into particle fractions.

18. The method as recited in claim 1 wherein the second layer of CRUD has a lower porosity than the first layer of CRUD.

19. The method as recited in claim 18 wherein the first layer of CRUD is fluffy CRUD and the second layer of CRUD is tenacious CRUD.

\* \* \* \* \*